United States Patent [19]

Lannert et al.

[11] Patent Number: 4,485,049
[45] Date of Patent: Nov. 27, 1984

[54] TWO-STAGE CRYSTALLIZATION OF NITRILOTRIACETONITRILE FROM A HOT SOLUTION

[75] Inventors: Kent P. Lannert, Freeburg, Ill.; Chung Y. Shen; Dat S. Trieu, both of St. Louis, Mo.

[73] Assignee: Monsanto Company, St. Louis, Mo.

[21] Appl. No.: 455,394

[22] Filed: Jan. 3, 1983

[51] Int. Cl.$^3$ ............................................ C07C 121/43
[52] U.S. Cl. ........................ 260/465.5 R; 260/465.5 A
[58] Field of Search .................. 260/465.5 R, 465.5 A

[56] References Cited

U.S. PATENT DOCUMENTS

| | | | |
|---|---|---|---|
| 2,405,966 | 8/1946 | Loder | 260/465.5 A |
| 3,862,203 | 1/1975 | Greco et al. | 260/465.5 A |
| 3,907,858 | 9/1975 | Davis et al. | 260/465.5 A |
| 3,925,448 | 12/1975 | Lanier | 260/465.5 A |
| 3,959,342 | 5/1976 | Homberg et al. | 260/465.5 A |

*Primary Examiner*—Joseph Paul Brust
*Attorney, Agent, or Firm*—J. H. Beusen; J. C. Logomasini; A. H. Cole

[57] ABSTRACT

A process is disclosed for producing crystalline nitrilotriacetonitrile from a solution of nitrilotriacetonitrile and water in excess of 95° C., comprising:

a. cooling the nitrilotriacetonitrile-water solution in a first stage to the range of about 70° C. to about 90° C., preferably from about 80° C. to about 90° C., and more preferably about 85° C., to produce a nitrilotriacetonitrile water slurry; and b. further cooling the nitrilotriacetonitrile-water slurry in a second stage to below about 35° C., carried out either continuously or in a batch process. Cooling in the first stage is preferably accomplished by recycling cooled nitrilotriacetonitrile-water slurry from the second stage. Cooling in the second stage is preferably accomplished by vacuum cooling.

15 Claims, No Drawings

TWO-STAGE CRYSTALLIZATION OF NITRILOTRIACETONITRILE FROM A HOT SOLUTION

FIELD OF THE INVENTION

This invention relates to the crystallization of nitrilotriacetonitrile from a hot aqueous solution of nitrilotriacetonitrile, such as the solution resulting from production of nitrilotriacetonitrile.

BACKGROUND

Nitrilotriacetonitrile is produced by reacting an aqueous mixture of either ammonia or an equivalent ammonium salt, or hexamethylenetetramine with formdaldehyde and hydrogen cyanide in the presence of a strong mineral acid. Most nitrilotriacetonitrile has been produced at temperatures below 95° C. At these temperatures, a concentrated reaction mixture exists as a dispersion of nitrilotriacetonitrile in water. Above 95° C., nitrilotriacetonitrile and water form a homogeneous phase. Running the reaction above 95° C. results in a reduced reaction time and can minimize difficulties in handling the dispersion. However, crystallization of the nitrilotriacetonitrile from reaction mixtures above 95° C. has proven to be a problem.

When the reaction has been run at temperatures below 95° C., the procedure has been to cool the reaction mixture rapidly in one step to 25°-30° C. This procedure has produced crystals that could be filtered and handled using normal production separation equipment. However, when reaction mixtures in excess of 95° C. are rapidly cooled in one step to 25° C. to 30° C., the crystals produced are very small, are difficult to separate from the mother liquor and are difficult to wash, and can plug filters and lines. A crystallization process that produces large easily filterable crystals from nitrilotriacetonitrile reaction mixture when cooled from temperatures in excess of 95° C. would be an advancement in the art.

SUMMARY OF THE INVENTION

This invention provides a process for producing crystalline nitrilotriacetonitrile from a solution of nitrilotriacetonitrile and water in excess of 95° C., comprising:

a. feeding the nitrilotriacetonitrile-water solution to a first stage where it is being cooled to the range of about 70° C. to about 90° C., with a sojourn time at this first stage of at least about 5 minutes to produce a nitrilotriacetonitrile-water slurry; and b. further cooling the nitrilotriacetonitrile-water slurry in a second stage to below about 35° C.

DESCRIPTION OF THE PREFERRED EMBODIMENTS

Crystalline nitrilotriacetonitrile produced from a nitrilotriacetonitrile-water mixture at a temperature in excess of 95° C. that is rapidly cooled in one step to 25° C. to 35° C. tends to produce very fine crystals that are difficult to separate from the nitrilotriacetonitrile mother liquor, and are difficult to wash. This results in a product that is more contaminated with the components of the mother liquor. Additionally, a dispersion containing a large amount of fine crystals is difficult to handle, is difficult to pump, and has a tendency to plug lines.

It has been found that larger and more uniform crystals are produced if the high temperature nitrilotriacetonitrile-water mixture is cooled in two stages to form the crystalline nitrilotriacetonitrile.

Temperature of the first stage must be about 70° C. to about 90° C., preferably about 80° C. to about 90° C., and more preferably about 85° C. At temperatures in excess of about 90° C., insufficient crystal formation occurs in the first stage, leaving a large proportion of nitrilotriacetonitrile in solution going into the second stage. When this more concentrated solution is cooled in the second stage, an unacceptable percentage of fine crystals is formed. At temperatures below about 70° C., excess nucleation occurs in the first stage, also resulting in formation of an excess number of fine crystals.

The sojourn time in the first stage must be at least about 5 minutes, preferably at least about 10 minutes, and most preferably at least about 15 minutes. The sojourn time is defined in continuous crystallization equipment as the volume of the first stage reactor divided by the feed rate, and in batch crystallization processes as the time period beginning with the commencement of cooling to the first stage temperature and ending with the commencement of cooling to the second stage temperature.

Sojourn time less than about 5 minutes provides an insufficient amount of time for crystal formation in the first stage, resulting in formation of an unacceptable number of fine crystals in the second stage. Longer sojourn times reduce the capacity of the crystallization equipment. Sojourn time in excess of about 30 minutes is generally not necessary.

In the first stage, the cooling should be as rapid as possible. A preferred method is direct cooling by recycling the cooled slurry from the second stage into the first stage in the proper proportion to produce the desired temperature. This recycled slurry also seeds the solution, resulting in larger, more uniform crystals. An acceptable, but less preferred method is use of cooling coils or cooling jackets. This method is less preferred due to riming that can occur on the cold surfaces. Vacuum cooling is another acceptable method, but is less preferred due to difficulty of condensing the vapors produced and due to foaming that can occur. The nitrilotriacetonitrile-water mixture should be agitated for uniformity of temperature. However, high agitation and recirculation can result in foaming, crystal breakage, and increased nucleation. Crystal breakage and excessive nucleation can result in formation of an undesirable number of fine crystals. Agitation and recirculation should be controlled to minimize these effects. It is preferred that at least about 50% of the total nitrilotriacetonitrile be present as crystals at the completion of the first stage. It is also preferred that the high temperature nitrilotriacetonitrile solution be fed to the first stage over a period of time, during the first stage cooling.

Cooling in the second stage can also be rapid. However, cooling methods in this stage are more flexible. A preferred method is vacuum cooling. This method is preferred because, in addition to being an efficient cooling method, it also serves to improve the yield during the crystallization step by concentrating the solution, and removes any gaseous hydrogen cyanide that might present a later safety problem. Other suitable methods of cooling include cooling jackets and coils, and recycling of cooled mother liquor resulting from separation of the crystalline nitrilotriacetonitrile back into the second stage. The temperature should be below 35° C., preferably below 30° C., and particularly below about 25° C. This temperature range is sufficient for a good yield of crystals. Some riming can occur in the second stage, but this can be minimized by coating the cool surfaces in the crystallizer with a nonstick coating, such as a fluorocarbon polymer.

The sojourn time in stage two is less critical than in stage one. However, the mixture must remain in stage two for a sufficient time to complete formation of crystals. Stage two should also be agitated to keep crystals in suspension.

This process is preferably carried on as a continuous process using two continuous crystallization tanks, one for stage one and one for stage two. Additionally, multiple tanks could be used for either stage one, stage two or both. This process can also be adapted for use in single tank batch crystallization provided that the tank is adapted for feeding of the nitrilotriacetonitrile solution during first stage cooling to the desired temperature with the desired sojourn time, and is also adapted to further cooling for stage two.

The following Examples serve to illustrate the process of this invention. They are intended as illustrative only and are not intended in any way to limit the scope of this invention. All parts and percentages are by weight unless otherwise specified.

EXAMPLE 1

Nitrilotriacetonitrile was produced from hexamethylenetetramine, formaldehyde and hydrogen cyanide, at a temperature of 115° C. In the first run, the reaction solution was collected in a receiver cooled in a bucket of ice and water. In run two, the reaction product was collected at 90° C. and was thereafter cooled to ambient temperatures by vacuum cooling. The crystal size distribution for each of the runs was determined by measuring the weight percent of the crystals that was retained on each of a series of progressively finer standard screens. These results, and a comparison with Run 3, in which nitrilotriacetonitrile is produced at 80° C. and cooled in one step to 25° C.–30° C., are shown in Table I.

TABLE I

| | Crystal Size Distribution (%) | | |
|---|---|---|---|
| USS Mesh | Run 1 | Run 2 | Run 3 |
| +20 | 0 | 12 | 1 |
| −20 + 50 | 0 | 31 | 71 |
| −50 + 100 | 3.5 | 51 | 14 |
| −100 + 120 | 3.5 | 4 | 1 |
| −120 | 93 | 2 | 13 |

EXAMPLE 2

A 33% solution of nitrilotriacetonitrile and water was prepared and heated to approximately 100° C. This solution was fed into a first stage crystallizer at a controlled rate. The first stage crystallizer was a small tank equipped with an agitator and with a overflow pipe through which the nitrilotriacetonitrile-water mixture flowed into a second stage crystallizer. The second stage crystallizer was a water jacketed tank equipped with an agitator. A recirculation pump drew the nitrilotriacetonitrile-water mixture from the second stage crystallizer and circulated part of this mixture to a product collector, part to the first stage crystallizer to provide cooling, and part to the second stage crystallizer. Samples of the product were subject to Accumulative Screen Analysis, and the mean crystal size of each run was determined from these results. The temperature of the first stage crystallizer, the sojourn time in the first stage crystallizer and the resulting mean crystal size in millimeters are shown in Table II. This compares to nitrilotriacetonitrile that is crystallized in one step from an 80° C. reaction mixture to 25° C.–30° C., which has a mean crystal size of 0.134 millimeters.

TABLE II

| Average Crystal Size with Respect to First Stage Temperature and Sojourn Time | | | |
|---|---|---|---|
| Run No. | Temp °C. First Stage | Sojourn Time-Mins. First Stage | Mean Crystal Size mm |
| 1 | 80 | 17 | 0.11 |
| 2 | 80 | 13.3 | 0.10 |
| 3 | 85 | 13.3 | 0.114 |
| 4 | 85 | 17 | 0.132 |
| 5 | 85 | 17 | 0.143 |
| 6 | 85 | 20 | 0.146 |
| 7 | 90 | 20 | 0.120 |

EXAMPLE 3

About 255 ml of a 33% solution of nitrilotriacetonitrile was prepared and heated to approximately 100° C. This solution was fed into a first stage crystallizer at about 15 ml/min. The first stage crystallizer was a 400 ml stainless steel beaker with good agitation. The first stage crystallizer initially contained about 35 ml of 33% nitrilotriacetonitrile slurry at the desired temperature. The temperature of the first stage crystallizer was maintained at the desired temperature by a water bath. When feeding of the nitrilotriacetonitrile was completed, the beaker and its contents were cooled to about 25° C. in an ice-water bath. Additionally, one run was done in which the 100° C. solution was cooled to 25° C. in one stage. Mean crystal sizes for each of the runs was determined in Example 2. The results are shown in Table III.

TABLE III

| Mean Crystal Size with Respect to First Stage Temperature | | |
|---|---|---|
| Run No. | Temp. °C. First Stage | Mean Crystal Size mm |
| 8 | 80 | .115 |
| 9 | 70 | .112 |
| 10 | 65 | .087 |
| 11 | 60 | .080 |
| 12 | 25 | .074 |

A comparison of runs 1, 2 and 8 shows that the results of Examples 2 and 3 are quite comparable even though Example 2 uses a continuous process, and Example 3 uses essentially a batch process, and even though there are other differences in procedure and apparatus.

In order to filter the crystalline nitrilotriacetonitrile, the crystals should have a mean crystal size in excess of about 0.11 mm, preferably in excess of about 0.12 mm, and more preferably in excess of about 13 mm. From the results of Examples 2 and 3, the first stage crystallization must occur in a temperature range above about 70° C. to produce a mean crystal in excess of about 0.11 mm. To produce a mean crystal in excess of about 0.12 mm, the first stage crystallization must occur at about 80° C. to about 90° C. And, to produce a mean crystal size in excess of about 0.13 mm, the first stage crystallization must occur at about 85° C.

What is claimed is:

1. A two-stage process for producing crystalline nitrilotriacetonitrile from a solution of nitrilotriacetonitrile and water in excess of 95° C., comprising:
   a. feeding the nitrilotriacetonitrile-water solution to a first stage where it is being cooled to the range of about 70° C. to about 90° C. with a sojourn time at this first stage, at least about 10 minutes to produce a nitrilotriacetonitrile-water slurry; and
   b. further cooling the nitrilotriacetonitrile-water slurry in a second stage to below 35° C. wherein vacuum cooling is employed in said second stage.

2. The process of claim 1 in which the process is carried on as a continuous crystallization process.

3. The process of claim 2 wherein the nitrilotriacetonitrile-water solution is the reaction mixture in which the nitrilotriacetonitrile is produced.

4. The process of claim 2 wherein the first stage temperature range is from about 80° C. to about 90° C.

5. The process of claim 2 wherein the first stage temperature is about 85° c.

6. The process of claim 2 wherein the first stage sojourn time is at least 10 minutes.

7. The process of Claim 2 wherein the first stage cooling is accomplished by recycling cooled nitrilotriacetonitrile-water mixture from the second stage.

8. The process of claim 2 wherein the second stage cooling is accomplished solely by vacuum cooling.

9. The process of claim 1 wherein the process is carried on as a batch crystallization process.

10. The process of claim 9 wherein the nitrilotriacetonitrile-water solution is the reaction mixture in which the nitrilotriacetonitrile is produced.

11. The process of claim 9 wherein the first stage temperature range is from about 80° C. to about 90° C.

12. The process of claim 9 wherein the first stage temperature is about 85° C.

13. The process of claim 9 wherein the first stage sojourn time is at least 10 minutes.

14. The process of claim 9 wherein the first stage cooling is accomplished by recycling cooled nitrilotriacetonitrile-water mixture from the second stage.

15. The process of claim 9 wherein the second stage cooling is accomplished solely by vacuum cooling.

* * * * *